(12) United States Patent
Takeda et al.

(10) Patent No.: US 8,000,800 B2
(45) Date of Patent: Aug. 16, 2011

(54) CONTACTLESS CHARGING SYSTEM FOR AN ARTIFICIAL ORGAN, A STORAGE DEVICE AND A FEEDING DEVICE FOR USE WITH THIS SYSTEM

(75) Inventors: Harumi Takeda, Osaka-fu (JP); Takahiro Hirakawa, Ibaraki-ken (JP)

(73) Assignee: Limited Company TM, Osaka (JP)

( * ) Notice: Subject to any disclaimer, the term of this patent is extended or adjusted under 35 U.S.C. 154(b) by 1115 days.

(21) Appl. No.: 10/514,502

(22) PCT Filed: May 22, 2003

(86) PCT No.: PCT/JP03/06430
§ 371 (c)(1), (2), (4) Date: Nov. 15, 2004

(87) PCT Pub. No.: WO03/100942
PCT Pub. Date: Dec. 4, 2003

(65) Prior Publication Data
US 2005/0165461 A1 Jul. 28, 2005

(30) Foreign Application Priority Data
May 23, 2002 (JP) ................................. 2002-148908

(51) Int. Cl.
*A61N 1/378* (2006.01)
(52) U.S. Cl. .......................................... 607/61; 607/60
(58) Field of Classification Search .................... 607/61, 607/60; 623/3.27
See application file for complete search history.

(56) References Cited

U.S. PATENT DOCUMENTS

| 3,942,535 | A | | 3/1976 | Schulman | |
|---|---|---|---|---|---|
| 5,314,453 | A | * | 5/1994 | Jeutter | 607/61 |
| 5,690,693 | A | * | 11/1997 | Wang et al. | 607/61 |
| 5,769,877 | A | * | 6/1998 | Barreras, Sr. | 607/61 |
| 6,088,619 | A | | 7/2000 | Hein et al. | |
| 6,138,681 | A | * | 10/2000 | Chen et al. | 128/899 |
| 6,400,991 | B1 | * | 6/2002 | Kung | 607/61 |
| 6,546,268 | B1 | * | 4/2003 | Ishikawa et al. | 600/345 |
| 6,553,263 | B1 | * | 4/2003 | Meadows et al. | 607/61 |

(Continued)

FOREIGN PATENT DOCUMENTS

DE 2616297 A1 10/1976

(Continued)

OTHER PUBLICATIONS

Translation of International Preliminary Examination Report for PCT/JP2003/006430 completed Apr. 13, 2004.

(Continued)

*Primary Examiner* — Niketa I Patel
*Assistant Examiner* — Rex Holmes
(74) *Attorney, Agent, or Firm* — Cheng Law Group, PLLC (57) ABSTRACT

According to a charging system of this invention, an alternating current required for charging of an electric double layer capacitor of a storage device in the body may be transmitted from a feeding device outside the body through power receiving and power transmitting coils. The electric double layer capacitor may be charged in a contactless mode, without incising the body of the artificial organ user, while the storage device remains embedded in the body. The electric double layer capacitor may be charged reliably by avoiding a shortage of charging since the charge status of the electric double layer capacitor of the storage device is known during a charging operation.

15 Claims, 8 Drawing Sheets

U.S. PATENT DOCUMENTS 6,695,885 B2 * 2/2004 Schulman et al. .............. 623/25

FOREIGN PATENT DOCUMENTS

| WO | WO-94/25105 A1 | 11/1994 |
| WO | WO-96/20754 A1 | 7/1996 |
| WO | WO-96/40367 A1 | 12/1996 |
| WO | WO-98/02980 A1 | 1/1998 |
| WO | WO-99/18879 A1 | 4/1999 |
| WO | WO-00/66221 A1 | 11/2000 |

OTHER PUBLICATIONS

International Search Report for PCT/JP03/06430 mailed on Jun. 24, 2003.

International Preliminary Examination Report for PCT/JP03/06430 completed on Apr. 13, 2004.

Supplementary European Search Report for the Application No. EP 03 73 0594 dated Sep. 1, 2008.

* cited by examiner

| charge voltage range (volt) | number of pulses | charge voltage range (volt) | number of pulses |
|---|---|---|---|
| 0~V1 | 1 | V4~V5 | 5 |
| V1~V2 | 2 | V5~V6 | 6 |
| V2~V3 | 3 | V6 - below 2.3 | 7 |
| V3~V4 | 4 | 2.3 or higher | 8 |

0 volt < V1<V2<V3<V4<V5<<6 <2.3 volts

| output voltage range volt | coil displacement range | resistance of digital variable resistor | resonant condition |
|---|---|---|---|
| v1~v2 | Q1 or more | resistance 1 | resonant condition 1 |
| v2~v3 | Q1~Q2 | resistance 2 | resonant condition 2 |
| v3~v4 | Q2~Q3 | resistance 3 | resonant condition 3 |
| v4~v5 | Q3~Q4 | resistance 4 | resonant condition 4 |
| v5 or higher | below Q4 | resistance 5 | resonant condition 5 | v1<v2<v3<v4<v5, Resonant condition 1 is close to absolutely non-resonant con
Q4<Q3<Q2<Q1

Fig.8

| output voltage range of voltage smoothing circuit 17 (volt) | output voltage range of voltage smoothing circuit 14 (volt) | coil displacement range Q(mm) |
|---|---|---|
| v1~v2 | va~vb | Q1 or more |
| v2~v3 | vb~vc | Q1~Q2 |
| v3~v4 | vc~vd | Q2~Q3 |
| v4~v5 | vd~ve | Q3~Q4 |
| v5 or higher | ve or higher | below Q4 |

| type of identifying coil | number of pulses |
|---|---|
| coil 19A | 10 |
| coil 19B | 11 |
| coil 19C | 12 |
| coil 19D | 13 |

Fig.14

CONTACTLESS CHARGING SYSTEM FOR AN ARTIFICIAL ORGAN, A STORAGE DEVICE AND A FEEDING DEVICE FOR USE WITH THIS SYSTEM

TECHNICAL FIELD

This invention relates to a charging system for an artificial organ having a storage device embedded in the body along with the artificial organ to act as an artificial organ driving power source, and a feeding device for feeding power to the storage device, and particularly to a technique for enabling a reliable charging in a contactless mode of the storage device remaining embedded in the body.

BACKGROUND ART

Conventionally, a cardiac pacemaker (hereinafter referred to simply as "pacemaker" where appropriate) exists as one of the artificial organs. The pacemaker is embedded in the body with a battery acting as driving power source. The pacemaker embedded in the body, while receiving a supply of driving electric power from the battery, causes the heart to beat regularly by directly applying an electrical pulse to and stimulating the heart. A nickel cadmium cell, lithium cell or the like is used for the battery acting as the driving power source of the cardiac pacemaker. The pacemaker maker continues applying an electrical pulse to the heart until the life of the battery runs out.

However, in the case of the above conventional example, there is a problem that the battery cannot be charged from outside the body while the battery remains embedded in the body. That is, since the battery remaining embedded in the body cannot be charged, when the life of the battery runs out, it is necessary to perform an operation to incise the body of the user of the artificial cardiac pacemaker, take the battery out of the body, and embed a new battery as replacement. However, the battery changing operation for incising the body imposes a heavy burden especially on a person having trouble with the heart.

This invention has been made having regard to the state of the art noted above, and its object is to provide a contactless charging system for an artificial organ, and a storage device and a feeding device for use with this system, in which the storage device embedded in the body along with the artificial organ to act as an artificial organ driving power source, while remaining embedded in the body, may be charged reliably in a contactless mode from outside the body (without incising the body).

DISCLOSURE OF THE INVENTION

A contactless charging system for an artificial organ, according to this invention, is characterized by comprising a storage device embedded as a whole in a body along with the artificial organ, and including power receiving coil means acting as a secondary side coil in a pair of coil means for transferring power, rectifying means for rectifying and outputting an AC received by the power receiving coil means, storage means for storing output from the rectifying means as electric power for driving the artificial organ, charge status detecting means for detect a charge status of the storage means, and charge status transmitting means for transmitting outside the body the charge status detected by the charge status detecting means; and a feeding device provided separately from the storage device and disposed as a whole outside the body, and including power transmitting coil means acting as a primary side coil in said pair of coil means, AC output means for outputting the AC to the power transmitting coil means, charge status receiving means for receiving the charge status transmitted outside the body from said charge status transmitting means, and charge status informing means for informing the charge status received by the charge status receiving means.

According to the contactless charging system for an artificial organ of this invention, in time of charging by the contactless charging system for an artificial organ (hereinafter called simply "charging system" as appropriate), the feeding device provided separately from the storage device and disposed as a whole outside the body is used to charge the storage device embedded as a whole in the body along with the artificial organ, as follows.

The charging system is operated, by setting the power transmitting coil means of the feeding device acting as a primary side coil in the pair of coil means for transferring power, and the power receiving coil means of the storage device acting as a secondary side coil in the pair of coil means, so that the two coil means are capable of transferring power by electromagnetic coupling, electromagnetic induction or electromagnetic wave. Then, the AC required for the charging outputted from the AC output means of the feeding device is transmitted from the power transmitting coil means outside the body to the storage device inside the body. The AC transmitted from the power transmitting coil means is received by the power receiving coil means inside the body, rectified by the rectifying means, and then fed to the storage means. In the storage means, the output from the rectifying means is stored as artificial organ driving power.

On the other hand, the charge status of the storage means of the storage device is detected by the charge status detecting means, and transmitted outside the body by the charge status transmitting means. The charge status transmitted outside the body is received by the charge status receiving means of the feeding device, and is reported by the charge status informing means. The charge status of the storage means of the storage device is checked outside the body through the report on charge status. The charging will be completed when the charge status reaches a predetermined state.

As described above, the AC required for charging is transmitted from the power transmitting coil means outside the body acting as a primary side coil to the power receiving coil means inside the body acting as a secondary side coil, in the form of electromagnetic coupling, electromagnetic induction or electromagnetic wave. As a result, the storage means may be charged in a contactless mode from outside the body, without incising the body, while the storage device remains embedded in the body.

The charge status of the storage means in the storage device is detected in the storage device inside the body and transmitted outside the body, and is received and reported by the feeding device outside the body. Thus, the charge status of the storage means may be checked during charging. As a result, a shortage of charging is avoided and the storage means may be charged reliably.

In the contactless charging system for an artificial organ according to this invention, at least one of the storage device and the feeding device includes amount of coil displacement detecting means for detecting an amount of coil displacement as an extent of a displacement occurring between the power receiving coil means and the power transmitting coil means, and the feeding device includes amount of coil displacement informing means for informing the amount of coil displacement detected by the amount of coil displacement detecting means.

For example, the amount of coil displacement detecting means of the storage device includes a smoothing circuit for smoothing a voltage at opposite ends of the power receiving coil detecting means, and a secondary side control circuit for determining the amount of coil displacement based on a smoothed voltage value. The amount of coil displacement detecting means of the feeding device includes a smoothing circuit for smoothing a voltage at opposite ends of the power transmitting coil detecting means, and a primary side control circuit for determining the amount of coil displacement based on a smoothed voltage value.

That is, the amount of coil displacement between the power receiving coil means and power transmitting coil means is detected by the amount of coil displacement detecting means, and is reported by the amount of coil displacement informing means outside the body. It is thus possible to know the extent of the displacement between the power receiving coil means and power transmitting coil means. Since both coils can be set to proper positions by resetting both the coil means according to the extent of the displacement, charging of the storage device may be carried out efficiently.

In the contactless charging system for an artificial organ according to this invention, it is preferable that the amount of coil displacement detecting means is disposed in the storage device, the amount of coil displacement detected being transmitted outside the body along with the charge status by the charge status transmitting means. It is further preferable that display means is provided for displaying the amount of coil displacement and the charge status transmitted outside the body by the charge status transmitting means.

That is, the amount of coil displacement detecting means is disposed in the storage device, and the amount of coil displacement detected is transmitted outside the body along with the charge status by using the charge status transmitting means. It is thus possible to avoid complication of the device construction. By displaying the amount of coil displacement on the display means, a positional adjustment of the power receiving coil means and power transmitting coil means may be carried out easily for correction of the amount of coil displacement.

In the contactless charging system for an artificial organ according to this invention, it is preferable that at least one of the storage device and the feeding device includes direction of coil displacement detecting means for detecting a direction of coil displacement as an extent of a displacement occurring between the power receiving coil means and the power transmitting coil means, and that the feeding device includes direction of coil displacement informing means for informing the direction of coil displacement detected by the direction of coil displacement detecting means.

For example, the direction of coil displacement detecting means of the storage device includes a plurality of direction detecting coils arranged at predetermined intervals around the power receiving coil means, and a secondary side control circuit for determining the direction of coil displacement based on voltages values detected from the plurality of direction detecting coils. The direction of coil displacement detecting means of the storage device includes a plurality of direction detecting coils arranged at predetermined intervals around the power receiving coil means, and a primary side control circuit for determining the direction of coil displacement based on voltages values detected from the plurality of direction detecting coils.

The direction of coil displacement detecting means of the storage device may include a plurality of divided power receiving coil means arranged annularly, and a secondary side control circuit for determining the direction of coil displacement based on voltages values detected from the respective power receiving coil means. The direction of coil displacement detecting means of the storage device may include a plurality of divided power receiving coil means arranged annularly, and a primary side control circuit for determining the direction of coil displacement based on voltages values detected from the respective power receiving coil means.

With the above construction, the direction of coil displacement between the power receiving coil means and power transmitting coil means is detected by the direction of coil displacement detecting means, and is reported by the direction of coil displacement informing means outside the body. It is thus possible to know the direction of the displacement between the power receiving coil means and power transmitting coil means. Therefore, the displacement between the power receiving coil means and power transmitting coil means may be corrected easily.

In the contactless charging system for an artificial organ according to this invention, it is preferable that the direction of coil displacement detecting means is disposed in the storage device, the direction of coil displacement detected being transmitted outside the body along with the charge status by the charge status transmitting means. It is further preferable that display means is provided for displaying the direction of coil displacement and the charge status transmitted outside the body by said charge status transmitting means.

That is, the direction of coil displacement detecting means is disposed in the storage device, and the direction of coil displacement detected is transmitted outside the body along with the charge status by using the charge status transmitting means. It is thus possible to avoid complication of the device construction. By displaying the direction of coil displacement on the display means, a positional adjustment of the power receiving coil means and power transmitting coil means may be carried out easily for correction of the direction of coil displacement.

In the contactless charging system for an artificial organ according to this invention, it is preferable that the storage means of the storage device is a rechargeable battery or an electric double layer capacitor. Where, for example, an electric double layer capacitor is used, which is small but has a large capacity, it is compact and has a sufficient storage function, has a long life with little deterioration or the like by repeated charging, and moreover is low in heat generation. Thus, the storage means in the form of an electric double layer capacitor is better than other, rechargeable batteries and the like.

A storage device for use with a contactless charging system for an artificial organ according to this invention, preferably, is a storage device having the above-described construction. That is, the storage device may be used with the contactless charging system, such that the storage device acting as artificial organ driving power source is reliably chargeable in a contactless mode while remaining embedded in the body.

A feeding device for use with a contactless charging system for an artificial organ according to this invention, preferably, is a feeding device having the above-described construction. That is, the feeding device may be used with the contactless charging system, such that the storage device acting as artificial organ driving power source is reliably chargeable in a contactless mode while remaining embedded in the body.

BEST MODE FOR CARRYING OUT THE INVENTION

Modes for solving the problem of the prior art include the following.

An embodiment of this invention will be described hereinafter with reference to the drawings.

Figure 1:
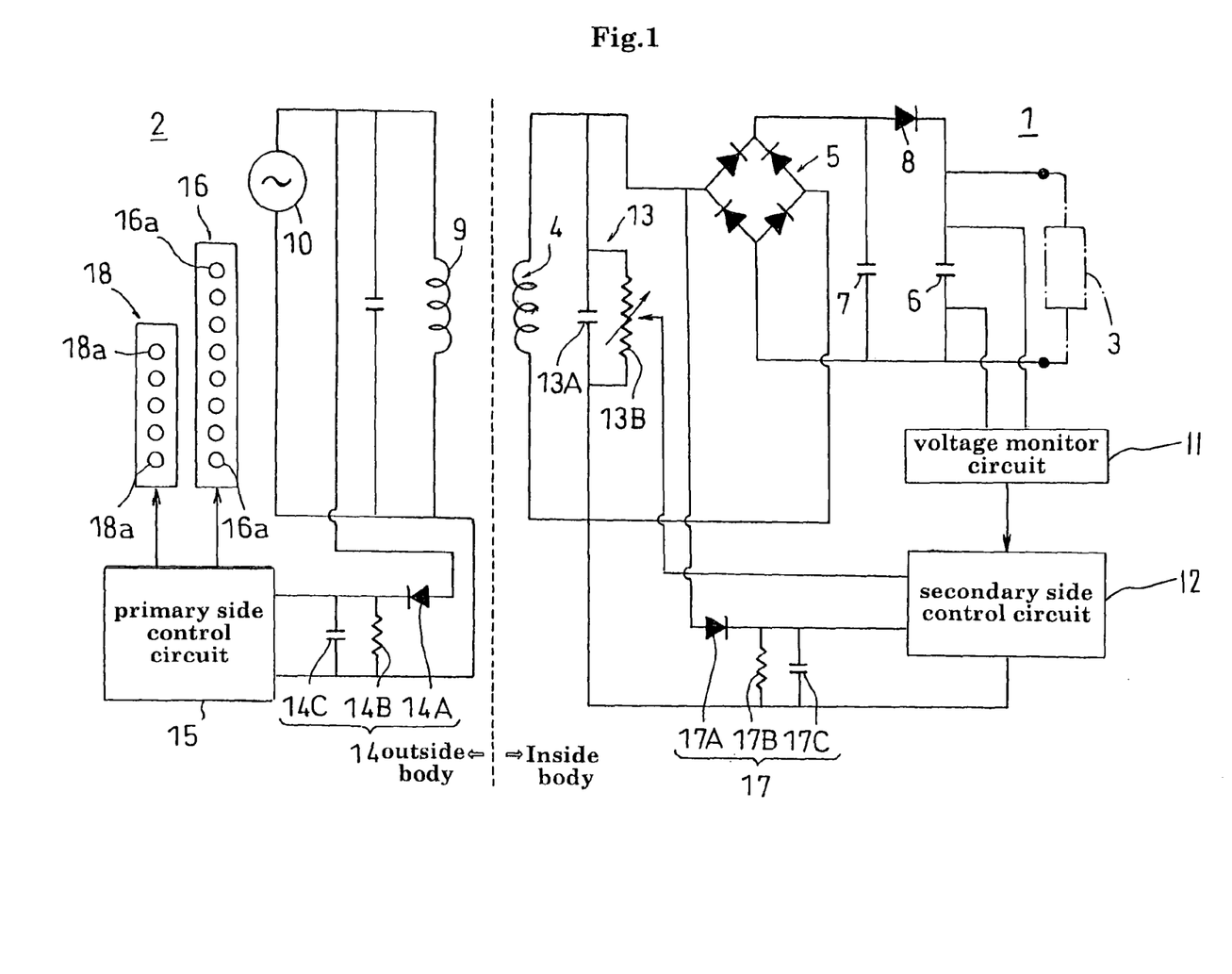
FIG. 1 is a block diagram showing an entire construction of a charging system according to an embodiment.
Figure 2:
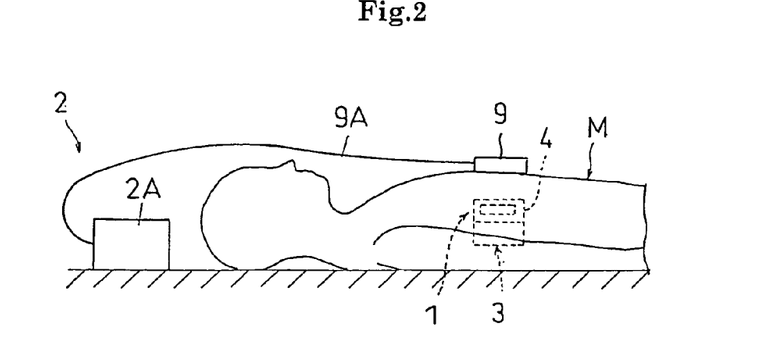
FIG. 2 is a schematic view showing a situation in time of charging by the charging system in the embodiment.

An embodiment of each of a contactless charging system for an artificial organ, and a storage device and a feeding device for use with this system, according to this invention, will be described hereinafter. FIG. 1 is a block diagram showing an entire construction of the charging system according to the embodiment. FIG. 2 is a schematic view showing a situation in time of charging by the charging system in the embodiment.

The charging system in the embodiment, as shown in FIGS. 1 and 2, includes a storage device 1 wholly embedded, as molded in a silicone resin or the like together with a cardiac pacemaker 3 acting as an artificial organ, for example, in the body of a user M of the pacemaker 3, and a feeding device formed separately from this storage device 1 and disposed as a whole outside the body of the user M carrying the pacemaker 3. In the body of the user M, the pacemaker 3, while receiving a supply of driving electric power from the storage device 1, causes the heart of the user M to continue beating regularly by directly applying an electrical pulse to and stimulating the heart.

The storage device 1 includes a power receiving coil (power receiving coil means) 4 acting as a secondary side coil in a pair of power transfer coils, a full wave rectification bridge (rectifying means) 5 for rectifying and outputting an AC received by the power receiving coil 4, and an electric double layer capacitor (storage means) 6 chargeable with the output from the full wave rectification bridge 5 to store pacemaker driving electric power. A ripple removing capacitor 7 and a reverse current preventing diode 8 are arranged between the full wave rectification bridge 5 and electric double layer capacitor (EDLC) 6.

The feeding device 2 includes a power transmitting coil (power transmitting coil means) 9 acting as a primary side coil in the pair of power transfer coils, an AC oscillator (AC output means) 10 for outputting an AC with a frequency of about 100 kHz to 2 GHz to this power transmitting coil 9. The power transmitting coil 9 is connected to a main body case 2A by a cable 9A to be freely movable. The power receiving coil 4 and power transmitting coil 9 usually have a diameter of about 20-50 mm, the power transmitting coil 9 being slightly larger.

When a charging operation is carried out by the charging system in the embodiment, the charging system is started after setting the power transmitting coil 9 of the feeding device 2 outside the body to a position opposed to the power receiving coil 4 of the storage device 1 inside the body so that the power receiving and power transmitting coils 4 and 9 may transfer power by electromagnetic coupling, electromagnetic induction or electromagnetic wave. Then, the AC required for the charging outputted from the AC oscillator 10 of the feeding device 2 is transmitted from the power transmitting coil 9 outside the body to the storage device 1 inside the body. The AC transmitted from the power transmitting coil 9 is received by the power receiving coil 4 inside the body, rectified by the full wave rectification bridge 5, and then fed to the electric double layer capacitor 6. In the electric double layer capacitor 6, pacemaker driving power is stored by the output from the full wave rectification bridge 5. The electric double layer capacitor (storage means) 6, although small, has a large capacity, therefore is compact and has a sufficient storage function, has a long life with little deterioration or the like by repeated charging, and moreover is low in heat generation. It is therefore better suited than other, rechargeable batteries and the like.

The storage device 1 includes a voltage monitor circuit (charge status detecting means) 11 for detecting a charge voltage indicative of a charge status of the electric double layer capacitor 6. This voltage monitor circuit 11 is arranged to output the detected charge voltage of the electric double layer capacitor 6 to a secondary side control circuit 12, and to stop the charging automatically when the charge voltage of the electric double layer capacitor 6 reaches 2.3V which is an operating voltage of the pacemaker 3. In this embodiment, the electric double layer capacitor 6 has a withstand voltage of 2.5V, and therefore an upper limit of the charge voltage of the electric double layer capacitor 6 is set to 2.3V which is a voltage below the withstand voltage.

The secondary side control circuit 12, as described hereinafter, acts as charge status transmitting means for cooperating with a resonance circuit 13 to transmit outside the body a charge status corresponding to the charge voltage detected by the voltage monitor circuit 11. The resonance circuit 13 is formed of the power receiving coil 4, and a capacitor 13A and a digital variable resistor 13B connected in parallel therewith. The power transfer action of the power receiving and power transmitting coils 4 and 9, essentially, is performed under resonant conditions. The digital variable resistor 13B is a resistor having a resistance discretely (stepwise) changeable by a digital signal outputted from the secondary side control circuit 12. A resonant condition caused by the resonance circuit 13 is changeable stepwise, with a change of the digital variable resistor 13B, from a full resonant condition to a virtually absolutely non-resonant condition. This change in the resonant condition on the secondary side by the resonance circuit 13 is transmitted from the power receiving coil 4 to the primary side through the power transmitting coil 9. A voltage at opposite ends of the power transmitting coil 9 varies according to levels of the resonant condition, and this is used to transmit the charge status of the electric double layer capacitor 6 outside the body.

Figure 3:
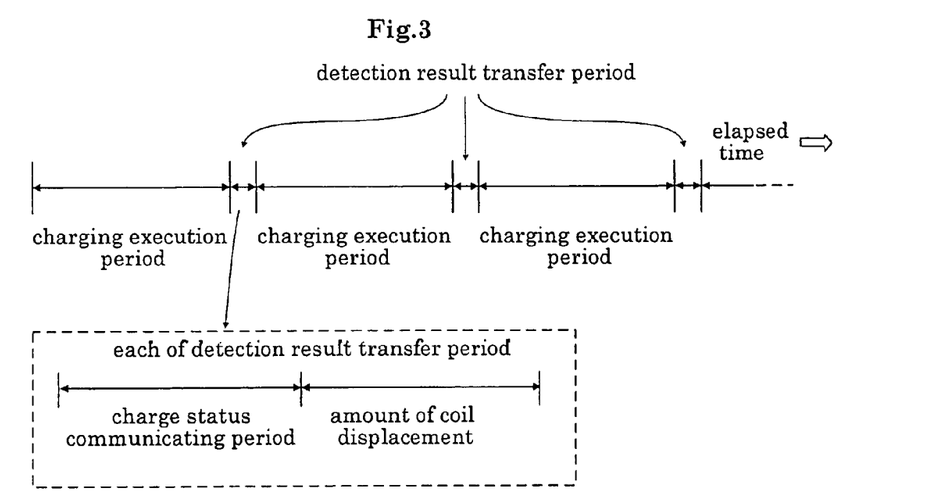
FIG. 3 is a time chart showing an allocation of detection result transfer periods in time of charging.

On the one hand, in the case of the charging process of the charging system according to the embodiment, as shown in FIG. 3, a detection result communicating period is set after every fixed charging period. The first half of the detection result communicating period is set as a charge status communicating period. And during a charging execution period, a digital signal is transmitted from the secondary side control circuit 12 to the variable resistor 13B to set a resistance to the digital variable resistor 13B to make the resonant condition by the resonance circuit 13 the full resonant condition over the entire period. During the charging execution period, charging power is transmitted efficiently with the resonant condition by the resonance circuit 13 in the full resonant condition over the entire period.

Figure 4:
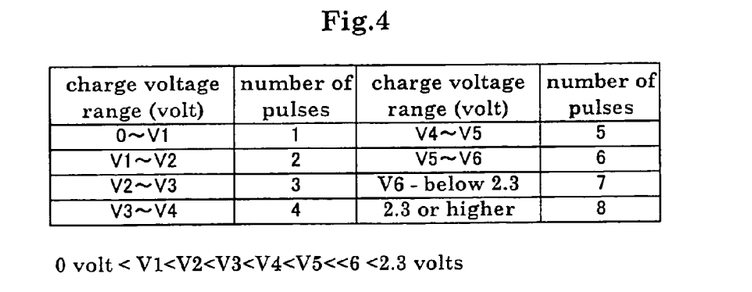
FIG. 4 is a table chart showing a relationship between charge voltage range and pulse ration number.

On the other hand, in the secondary side control circuit 12, as shown in FIG. 4, the charge voltage range (0V -2.3V) of the electric double layer capacitor 6 is divided into eight stages corresponding to the numbers of pulses 1 to 8, and a charge status is transmitted outside the body from inside the body by transmitting to the feeding device 2 the number of pulses corresponding to the charge voltage of the electric double layer capacitor 6 detected by the voltage monitor circuit 11 during one charge status communicating period. Specifically, during one charge status communicating period, a circuit operation, in which a digital signal is transmitted from the secondary side control circuit 12 to the digital variable resistor 13B so that the variable resistor 13B has a resistance to make the resonant condition by the resonance circuit 13 the absolutely non-resonant condition only for a predetermined short period of time, is repeated so that the number of pulses corresponding to the charge voltage may be outputted.

The charge status of the electric double layer capacitor 6 transmitted outside the body from inside the body in the form of pulse as described above, is detected based on a voltage change at the opposite ends of the power transmitting coil 9 of the feeding device 2 as described next. That is, a voltage at the opposite ends of the power transmitting coil 9 is detected by a voltage smoothing circuit 14 including a rectifier diode 14A, a resistance 14B and a capacitor 14C, and outputted to a primary side control circuit 15. The primary side control circuit 15, by detecting output changes of the voltage smoothing circuit 14, determines a charge status (number of pulses) of the storage device 1 during one charge status communicating period. In this embodiment, a pulse train transmitted from the storage device is smoothed, and the number of pulses is detected from its voltage value. However, the number of pulses may be counted directly.

Figure 5:
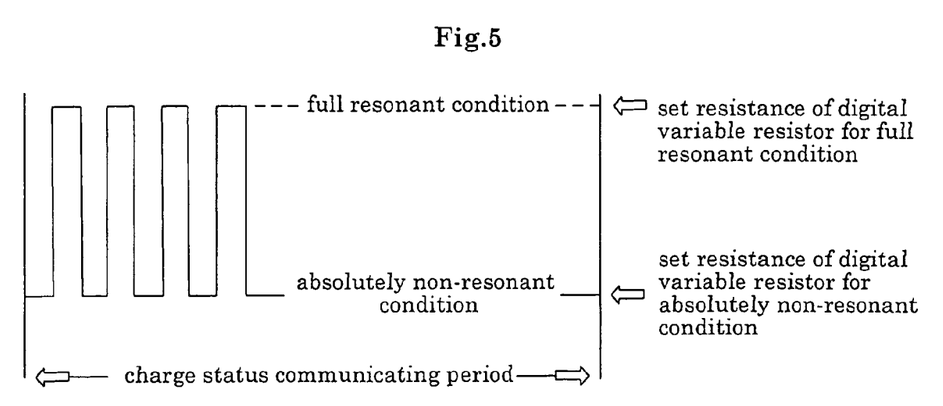
FIG. 5 is a time chart illustrating a transfer/detection situation of charge state in the embodiment.
Figure 6:
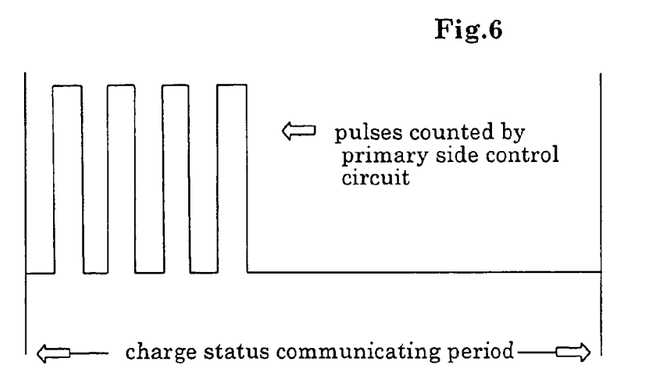
FIG. 6 is a time chart illustrating a transfer/detection situation of charge state in the embodiment.

When, as shown in FIG. 5, for example, during one charge status communicating period, switching to the absolutely non-resonant condition only for a fixed period of the resonant condition by the resonance circuit 13 is repeated four times, the primary side control circuit 15 counts four pulses as shown in FIG. 6. And when the primary side control circuit 15 counts eight pulses during one charge status communicating period, it is detected that the charge voltage of the electric double layer capacitor 6 has reached 2.3V, i.e. reached a full charge status. In the embodiment, therefore, the power transmitting coil 9, voltage smoothing circuit 14 and primary side control circuit 15 constitute a charge status receiving means for receiving a charge status of the electric double layer capacitor 6 transmitted outside the body from inside the body.

Further, the feeding device 2 includes a charge status display panel (charge status informing means) 16 disposed downstream of the primary side control circuit 15 for displaying, in real time, a charge status of the electric double layer capacitor 6. A charge status of the electric double layer capacitor 6 is notified by lighting the number of light emitting diodes 16a corresponding to the number of pulses counted by the primary side control circuit 15.

In the case of the charging system in the embodiment, as described hereinafter, the storage device 1 detects an amount of displacement between the power receiving and power transmitting coils 4 and 9 (amount of coil displacement), and transmits the detected amount of coil displacement outside the body through the power receiving and power transmitting coils 4 and 9 by varying the resonant condition by the resonance circuit 13 according the detected amount of coil displacement, as when transmitting the charge status of the electric double layer capacitor 6 outside the body. The transmission efficiency of charging power lowers in proportion to the amount of coil displacement between the power receiving and power transmitting coils 4 and 9, resulting in an extended charging time. For this reason, the displacement between the power receiving coil 4 and power transmitting coil 9 is detected and checked outside the body. The amount of coil displacement between the power receiving and power transmitting coils 4 and 9 and the power transmission efficiency between the power receiving and power transmitting coils 4 and 9 are in inversely proportional relationship. The larger amount of coil displacement results in the lower AC voltage produced at the opposite ends of the power receiving coil 4. That is, the voltage at the opposite ends of the power receiving coil 4 is inversely proportional to the amount of coil displacement.

In the storage device 1, the voltage at the opposite ends of the power receiving coil 4 corresponding to the amount of coil displacement is smoothed by a voltage smoothing circuit 17 including a rectifier diode 17A, a resistance 17B and a capacitor 17C, and its voltage value is detected by the secondary side control circuit 12. Thus, the voltage smoothing circuit 17 and secondary side control circuit 12 correspond to the amount of coil displacement detecting means in this invention.

Figure 7:
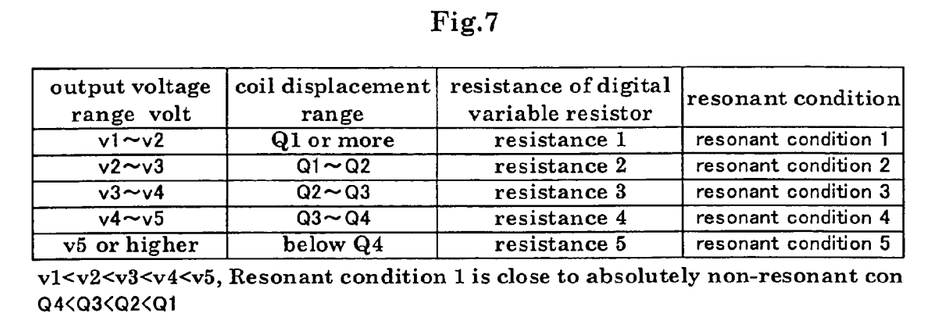
FIG. 7 is a table chart showing a relationship between factors on a secondary side relating to coil displacement.
Figure 8:
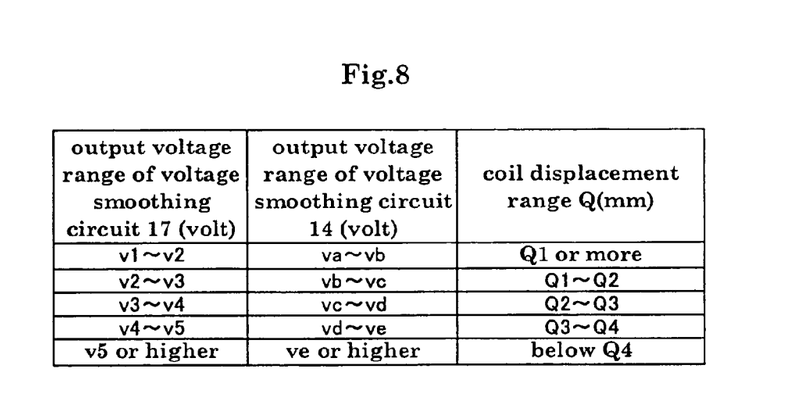
FIG. 8 is a table chart showing a relationship between primary side and secondary side relating to coil displacement.

On the one hand, in the secondary side control circuit 12, as shown in FIG. 7, the output voltage range of the voltage smoothing circuit 17 is divided beforehand into five stages, for example. The respective output voltage divisions have, assigned thereto in order from lowest voltage, five-stage resonance levels 1 to 5 set to rise successively stage by stage from the absolutely non-resonant condition. The resonance levels 1 to 5 are set so that voltage changes at the opposite ends of the power transmitting coil 9 occurring with changes between resonance level 5 and absolutely non-resonant condition are approximately half the voltage changes at the opposite ends of the power transmitting coil 9 occurring with the changes between the full resonant condition and absolutely non-resonant condition. This is done to facilitate a determination whether the voltage changes at the opposite ends of the power transmitting coil 9 are due to the communication of a charge status or due to the communication of an amount of coil displacement. Further, as shown in FIG. 7, in the secondary side control circuit 12, digital signals corresponding to the resistances of the digital variable resistor 13B in time of the five-stage resonant conditions 1-5 are set to correspond to the resonant conditions 1-5.

On the other hand, in the case of the charging process of the charging system in the embodiment, as shown in FIG. 3, the second half of the detection result communicating period is set as an amount of coil displacement communicating period. During the amount of coil displacement communicating period, the secondary side control circuit 12 recognizes a voltage division of the amount of coil displacement corresponding to a voltage detected by the voltage smoothing circuit 17. A digital signal is transmitted from the secondary side control circuit 12 to the digital variable resistor 13B so that the resonant condition by the resonance circuit 13 may be the resonant condition corresponding to the recognized voltage division. When, for example, the voltage detected by the voltage smoothing circuit 17 is recognized as voltage division (V3-V4), the resonance by the resonance circuit 13 is made the resonant condition 3.

And, as a change occurs in the resonant condition by the resonance circuit 13 on the secondary side, a phenomenon of a change in the voltage at the opposite ends of the power transmitting coil 9 also takes place in the feeding device 2 which is the primary side. Then, the feeding device 2 uses this phenomenon, and detects an amount of coil displacement between the power receiving and power transmitting coils 4 and 9 transmitted outside the body. The larger the amount of coil displacement is, the farther away the resonant condition of the resonance circuit 13 is from the full resonant condition. Therefore, the voltage at the opposite ends of the power transmitting coil 9 lowers in proportion to the amount of coil displacement.

Specifically, the voltage smoothing circuit 14 smoothes the voltage at the opposite ends of the power transmitting coil 9, and the primary side control circuit 15 checks its voltage value to detect the amount of coil displacement. In the case of the primary side control circuit 15, as shown in FIG. 1, the output voltage range of the voltage smoothing circuit 14 is divided into five stages to correspond to the divisions of the output voltage range of the voltage smoothing circuit 17 (i.e. amount of coil displacement Q). The primary side control circuit 15 checks a value of the voltage outputted from the voltage smoothing circuit 14, recognizes a division corresponding thereto, and detects an amount of coil displacement.

In addition to the above, the primary side control circuit 15 checks whether a change in the output voltage of the voltage smoothing circuit 14 is the same as or half a voltage change occurring with a change between the full resonant condition and absolutely non-resonant condition. If it is the same, it is recognized and processed as the communication of a charge status. If it is the half, it is recognized and processed as the communication of an amount of coil displacement. Thus, an arrangement is provided to avoid confusion.

The feeding device 2 includes an amount of coil displacement display panel (amount of coil displacement informing means) 18 disposed downstream of the primary side control circuit 15 for displaying an amount of coil displacement between the power receiving and power transmitting coils 4 and 9. An amount of coil displacement is notified by lighting the number of light emitting diodes 18a corresponding to the amount of coil displacement detected by the primary side control circuit 15. The light emitting diodes 18a correspond to the display means of this invention.

Figure 9:
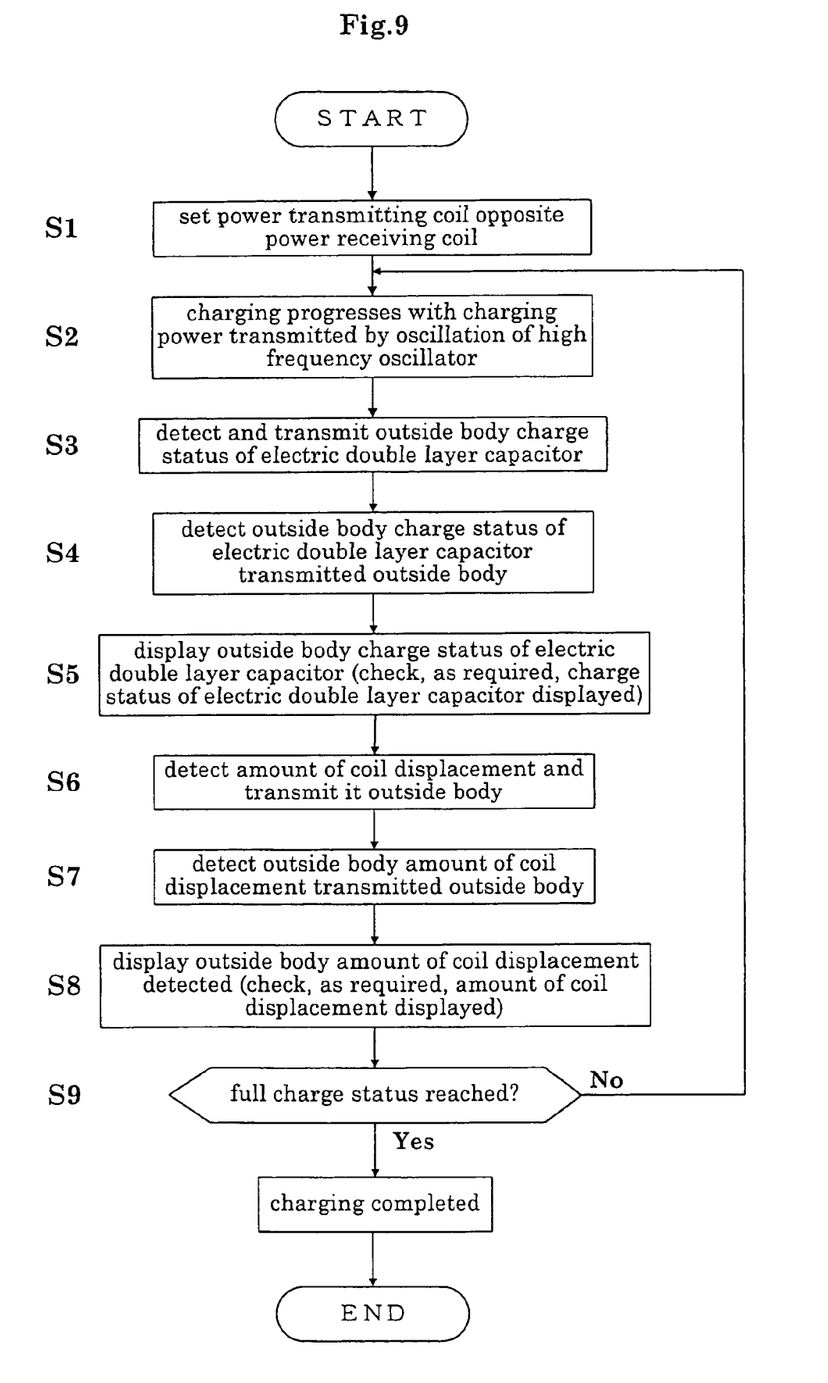
FIG. 9 is a flow chart showing a progress of charging by the charging system in the embodiment.

A situation occurring when the electric double layer capacitor 6 is charged by the charging system in the embodiment described above will now be described with reference to the drawings. FIG. 9 is a flow chart showing a progress of charging by the charging system in the embodiment.

[Step S1] The power transmitting coil 9 of the feeding device 2 outside the body is set to a position opposed to the power receiving coil 4 of the storage device 1 in the body.

[Step S2] The electric double layer capacitor 6 is charged as the AC oscillator 10 of the feeding device 2 starts oscillation to transmit charging electric power.

[Step S3] When a charge status communicating period comes up, the voltage monitor circuit 11, secondary side control circuit 12 and resonance circuit 13 cooperate to detect a charge voltage of the electric double layer capacitor 6 and transmit the number of pulses corresponding to the charge voltage outside the body from inside the body through the power receiving and power transmitting coils 4 and 9.

[Step S4] In the feeding device 2, the voltage smoothing circuit 14 and primary side control circuit 15 cooperate to detect the charge status of the electric double layer capacitor 6 transmitted outside the body as converted into the number of pulses.

[Step S5] The charge status display panel 16 of the feeding device 2 lights the number of light emitting diodes 16a corresponding to the charge status of the detected electric double layer capacitor 6.

[Step S6] When an amount of coil displacement communicating period comes up, the voltage smoothing circuit 17, secondary side control circuit 12 and resonance circuit 13 cooperate to detect an amount of coil displacement between the power receiving and power transmitting coils 4 and 9, and transmit it outside the body from inside the body through the power receiving and power transmitting coils 4 and 9.

[Step S7] In the feeding device 2, the voltage smoothing circuit 14 and primary side control circuit 15 detect the amount of coil displacement between the power receiving and power transmitting coils 4 and 9 transmitted outside the body.

[Step S8] The amount of coil displacement display panel 18 of the feeding device 2 lights the number of light emitting diodes 18a corresponding to the amount of coil displacement between the power receiving and power transmitting coils 4 and 9.

[Step S9] The charging operation is continued until the electric double layer capacitor 6 reaches a full charge status, and whenever a detection result communicating period comes up, steps S3-S8 are repeated to continue the process of detecting and informing the charge status and amount of coil displacement. During the charging operation, the operator (system driver) constantly checks the charge status of the electric double layer capacitor 6 on the charge status display panel 16. When the amount of coil displacement between the power receiving and power transmitting coils 4 and 9 displayed on the amount of coil displacement display panel 18 exceeds a predetermined amount, the coil displacement between the power receiving and power transmitting coils 4 and 9 is corrected to transmit the charging electric power efficiently. When the electric double layer capacitor 6 reaches the full charge status, the charging is completed to end the charging operation by the charging system.

Figure 10:
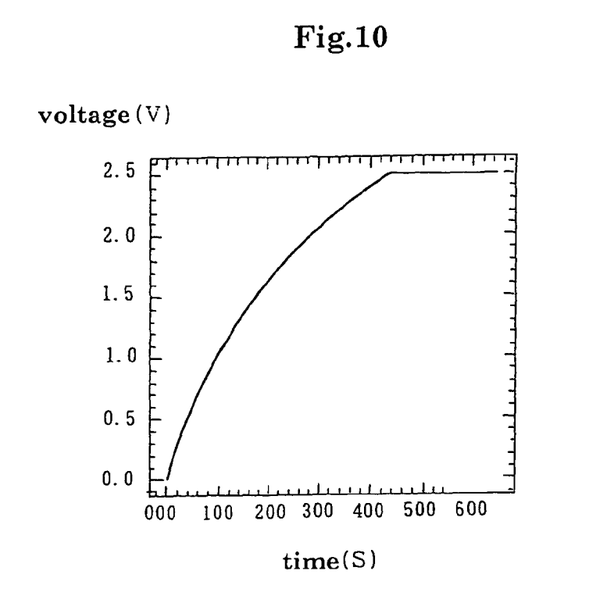
FIG. 10 is a graph showing changes with time of charge status by the charging system in a charging experiment.

In order to test the charging function of the charging system in the embodiment, a charging experiment has been conducted with a 10 mm thick piece of meat placed between the power receiving and power transmitting coils 4 and 9. The capacity of the electric double layer capacitor 6 is 1F. FIG. 10 shows variations with time of the charge voltage of the electric double layer capacitor 6 in the charging experiment. As shown in FIG. 10, the electric double layer capacitor 6 reached the full charge status of 2.3V 440 seconds from a start of charging.

Figure 11:
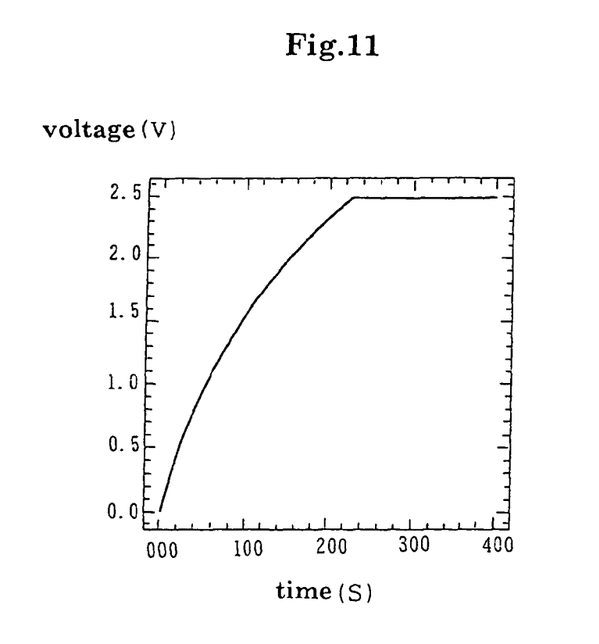
FIG. 11 is a graph showing changes with time of charge status by the charging system in a charging experiment.

For reference, a charging experiment has been conducted in the same way noted above except that a mere space is left, with no meat piece placed, between the power receiving and power transmitting coils 4 and 9. FIG. 11 shows variations with time of the charge voltage of the electric double layer capacitor 6 in this charging experiment. As shown in FIG. 11, the electric double layer capacitor 6 reached the full charge status of 2.3V 228 seconds from a start of charging.

From the above charging experiment, it has been confirmed that, in the case of the charging system in the embodiment, when an object of skin thickness is interposed between the power receiving and power transmitting coils 4 and 9, a charging function suited for practical use is fully demonstrated although the charging time is somewhat extended.

Thus, according to the charging system in the embodiment, the AC required for charging of the storage device 1 in the body may be transmitted from outside the body in the form of electromagnetic coupling, electromagnetic induction or electromagnetic wave. The electric double layer capacitor 6 may be charged in a contactless mode from outside the body, without incising the body, while the storage device 1 remains embedded in the body. Charging may be carried out reliably since the operator can check the charge status of the electric double layer capacitor 6 of the storage device 1 during a charging operation. In the case of the charging system in the embodiment, since the operator can know an amount of coil displacement between the power receiving and power transmitting coils 4 and 9, charging may be carried out efficiently by correcting the coil displacement between the power receiving and power transmitting coils 4 and 9.

A different embodiment of this invention will be described next. In a charging system according to the different embodiment, the storage device 1 detects a direction of displacement occurring between the power receiving coil 4 and power transmitting coil 9 (direction of coil displacement), and transmits it outside the body from inside the body. The feeding device 2 detects and informs the direction of coil displacement transmitted outside the body from inside the body. Since the other aspects are the same as in the preceding embodiment, common points will not be described and only different points will be described.

Figure 12:
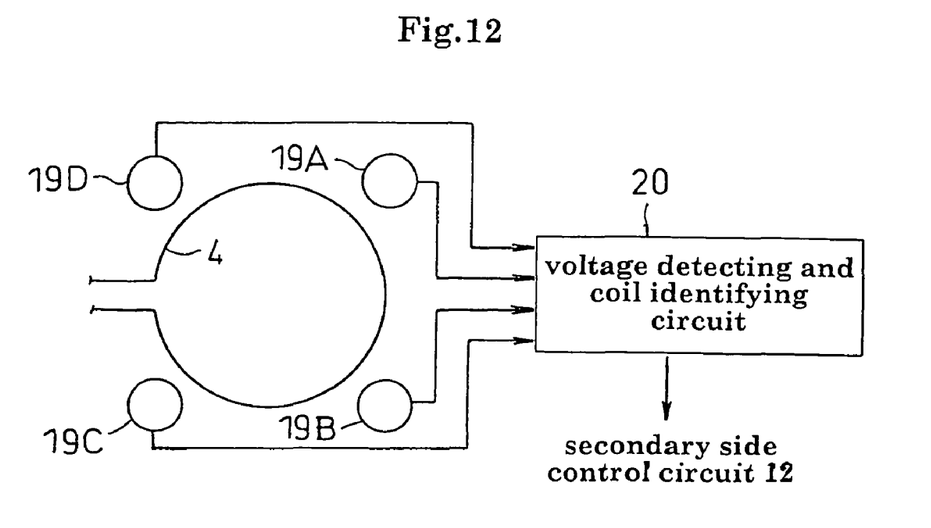
FIG. 12 is a block diagram showing a construction for detecting a direction of coil displacement in a charging system in another embodiment.

The charging system according to the different embodiment, as shown in FIG. 12, has four direction detecting coils 19A-19D arranged equidistantly at 90° intervals in the circumferential direction around the power receiving coil 4, and a voltage detecting and coil identifying circuit 20 for detecting voltages produced on the direction detecting coils 19A-19D as the charging electric power is transmitted from the power transmitting coil 9, comparing levels of the detected voltages of the direction detecting coils 19A-19D to identify a direction detecting coil located in a direction of displacement of the power transmitting coil 9, and outputting it as a direction of coil displacement to the secondary side control circuit 12. Differences in level among the detected voltages of the direction detecting coils 19A-19D are produced according to a direction of displacement of the power transmitting coil 9, and a direction of coil displacement is determined based on this. Therefore, the direction detecting coils 19A-19D and voltage detecting and coil identifying circuit 20 constitute the direction of coil displacement detecting means.

Figure 13:
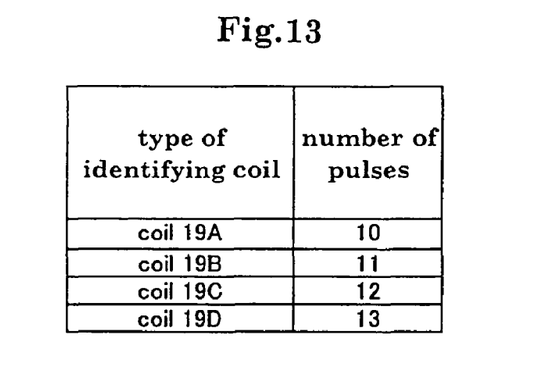
FIG. 13 is a table chart showing a relationship between direction of coil displacement and pulse ration number.
Figure 14:
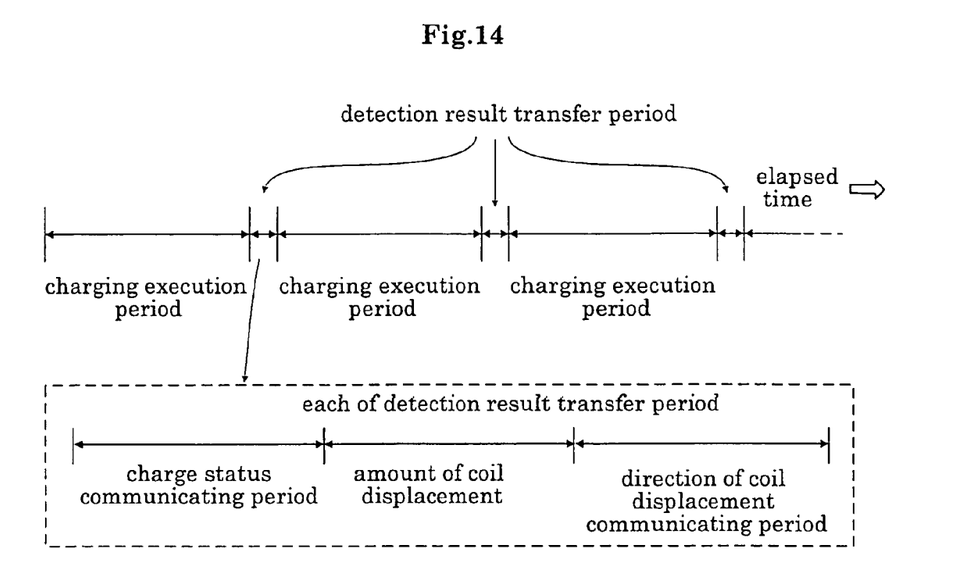
FIG. 14 is a time chart showing an allocation of direction of coil displacement transfer periods in time of charging.

In the secondary side control circuit 12, as shown in FIG. 13, numbers of pulses 10 to 13 are assigned to the respective direction detecting coils 19A-19D. During a direction of coil displacement communicating period added after the amount of coil displacement communicating period in the detecting result communicating period, as shown in FIG. 14, a coil outputted from the voltage detecting and coil identifying circuit 20 is transmitted outside the body from inside the body in a form converted into the number of pulses, as in the case of communicating the charge status of the electric double layer capacitor 6 outside the body.

On the other hand, in the feeding device 2, the voltage smoothing circuit 14 and primary side control circuit 15 count the number of pulses, detect a direction of coil displacement and report it on a direction of coil displacement display panel (not shown), as in the case of detecting the charge status of the electric double layer capacitor 6 transmitted outside the body.

In this embodiment, since the operator can know a direction of coil displacement between the power receiving and power transmitting coils 4 and 9, the coil displacement between the power receiving and power transmitting coils 4 and 9 may be corrected easily.

This invention is not limited to the above embodiments, but may be modified as follows:

(1) In both of the above embodiments, the storage means of the storage device 1 is the electric double layer capacitor 6. Instead of the electric double layer capacitor 6, various rechargeable batteries (e.g. lithium battery) may be used as the storage means.

(2) In both of the above embodiments, the resonant condition is changed by changing the resistance of a resistance element of the resonance circuit 13. The resonant condition may be changed by changing the capacity of a capacitative element (capacitor) of the resonance circuit 13.

(3) The charge status of the electric double layer capacitor 6, and the amount of coil displacement and the direction of coil displacement between the power receiving and power transmitting coils 4 and 9 are transmitted outside the body in the number of the pulses or the level of voltage in both of the above embodiments. Alternatively, they may be transmitted outside the body by using and coding a plurality of pulses continuous in time.

(4) A power transmitting coil 9 of large diameter may be installed on a bed in a hospital room, for charging the electric double layer capacitor 6 of the storage device 1 embedded in the body of a bedridden patient. In the other aspects, such a modified embodiment may be the same charging system as in both of the above embodiments.

(5) In both of the above embodiments, the charge status of the electric double layer capacitor 6, and the amount of coil displacement and the direction of coil displacement between the power receiving and power transmitting coils 4 and 9, are transmitted outside the body through the power receiving and power transmitting coils 4 and 9. A charging system, in which the charge status of the electric double layer capacitor 6, and the amount of coil displacement and the direction of coil displacement between the power receiving and power transmitting coils 4 and 9 are transmitted outside the body through two coils disposed independently of the power receiving and power transmitting coils 4 and 9 may be cited as a modified embodiment.

(6) In the example shown in FIG. 12, the four direction detecting coils 19A-19D are arranged around the power receiving coil 4 in order to detect a direction of coil displacement between the power receiving and power transmitting coils 4 and 9. Alternatively, for example, the power receiving coil 4 may be constructed of four divided coils. That is, with four divided power receiving coils are arranged adjacent each other in a plane, a displacement in a set position of the power transmitting coil 9 will cause an imbalance in the outputs of the four power receiving coils. Therefore, a direction of coil displacement between the four power receiving coils and power transmitting coils 9 may be known by comparing the levels of the outputs of these four power receiving coils.

(7) In both of the above embodiments, the artificial organ is a cardiac pacemaker. Artificial organs for which this invention is usable may be, not only a cardiac pacemaker, may be an artificial heart, artificial pancreas, and artificial urinary bladder, for example.

INDUSTRIAL UTILITY

As described above, a contactless charging system for an artificial organ, and a storage device and a feeding device for use with this system, according to this invention, are suitable for use with artificial organs such as a cardiac pacemaker, artificial heart, artificial pancreas, artificial urinary bladder and so on.

The invention claimed is:

1. A contactless charging system for an artificial organ, comprising:
   (A) a storage device adapted to be embedded as a whole in a body along with the artificial organ, and including a power receiving coil acting as a secondary side coil for transferring power, rectifying means for rectifying and outputting an alternating current received by the power receiving coil, storage means for storing output from the rectifying means as electric power for driving the artificial organ, charge status detecting means for detecting a charge status of the storage means, and charge status transmitting means for transmitting outside the body the charge status detected by the charge status detecting means; and
   (B) a feeding device provided separately from the storage device and disposed as a whole outside the body, and including a power transmitting coil acting as a primary side coil, AC output means for outputting the AC to the power transmitting coil, charge status receiving means for receiving the charge status transmitted outside the body from said charge status transmitting means, and charge status informing means for informing the charge status received by the charge status receiving means, wherein:
   each of the storage device and the feeding device includes amount of coil displacement detecting means for detecting an amount of coil displacement as an extent of a displacement occurring between the power receiving coil and the power transmitting coil, and the feeding device includes amount of coil displacement informing means for informing the amount of coil displacement detected by the amount of coil displacement detecting means;
   the amount of coil displacement detecting means of said storage device includes a smoothing circuit for smoothing a voltage at opposite ends of said power receiving coil, and a secondary side control circuit for determining the amount of coil displacement based on a smoothed voltage value;
   the amount of coil displacement detecting means of said feeding device includes a smoothing circuit for smoothing a voltage at opposite ends of said power transmitting coil, and a primary side control circuit for determining the amount of coil displacement based on a smoothed voltage value;
   the amount of coil displacement detecting means of said storage device is disposed in the storage device, a detection result communicating period is set after every fixed charging period of a plurality of fixed charging periods, and a circuit operation, in which a digital signal is transmitted from the secondary side control circuit to a digital variable resistor so that the digital variable resistor has a resistance to make a resonant condition by a resonance circuit a virtually absolutely non-resonant condition only for a predetermined short period of time, is repeated so that a number of divided pulses corresponding to a charge voltage and the digital signal may be transmitted outside the body by said charge status transmitting means after said every fixed charging execution period;
   display means adapted for displaying the amount of coil displacement divides and displays the amount of coil displacement transmitted outside the body by said charge status transmitting means based on an output voltage of the smoothing circuit provided with the primary side control circuit corresponding to an range of an output voltage of the smoothing circuit provided with the secondary side control circuit for every receiving signal of the amount of coil displacement; and
   the amount of coil displacement informing means informs said amount of coil displacement detected by the amount of coil displacement detecting means.

2. A contactless charging system for an artificial organ as defined in claim 1, wherein:
   at least one of the storage device and the feeding device includes direction of coil displacement detecting means for detecting a direction of coil displacement as an extent of a displacement occurring between the power receiving coil and the power transmitting coil, and the feeding device includes direction of coil displacement informing means for informing the direction of coil displacement detected by the direction of coil displacement detecting means.

3. A contactless charging system for an artificial organ as defined in claim 2, wherein:
   the direction of coil displacement detecting means of said storage device includes a plurality of direction detecting coils arranged at predetermined intervals around said power receiving coil, and a secondary side control circuit for determining the direction of coil displacement based on voltages values detected from the plurality of direction detecting coils.

4. A contactless charging system for an artificial organ as defined in claim 2, wherein:
   the direction of coil displacement detecting means of said storage device includes a plurality of direction detecting coils arranged at predetermined intervals around said power receiving coil, and a primary side control circuit for determining the direction of coil displacement based on voltages values detected from the plurality of direction detecting coils.

5. A contactless charging system for an artificial organ as defined in claim 2, wherein:
   the direction of coil displacement detecting means of said storage device includes a plurality of divided power receiving coils arranged annularly, and a secondary side control circuit for determining the direction of coil displacement based on voltages values detected from the respective power receiving coils.

6. A contactless charging system for an artificial organ as defined in claim 2, wherein:
   the direction of coil displacement detecting means of said storage device includes a plurality of divided power receiving coils arranged annularly, and a primary side control circuit for determining the direction of coil displacement based on voltages values detected from the respective power receiving coils.

7. A contactless charging system for an artificial organ as defined in claim 2, wherein:
   the direction of coil displacement detecting means is disposed in the storage device, the direction of coil displacement detected being transmitted outside the body along with the charge status by said charge status transmitting means.

8. A contactless charging system for an artificial organ as defined in claim 7, comprising:
   display means for displaying the direction of coil displacement and the charge status transmitted outside the body by said charge status transmitting means.

9. A contactless charging system for an artificial organ as defined in claim 1, wherein:
the charge status transmitting means of the storage device is arranged to transmit a result of detection of the charge status outside the body through the power receiving coil and the power transmitting coil acting as the pair of coils for transferring power.

10. A contactless charging system for an artificial organ as defined in claim 1, wherein:
the storage means of said storage device is a rechargeable battery.

11. A contactless charging system for an artificial organ as defined in claim 1, wherein:
the storage means of said storage device is an electric double layer capacitor.

12. A contactless charging system for an artificial organ, comprising:
(A) a storage device adapted to be embedded as a whole in a body along with the artificial organ, and including a power receiving coil acting as a secondary side coil in a pair of coils for transferring power, rectifying means for rectifying and outputting an alternating current received by the power receiving coil, storage means for storing output from the rectifying means as electric power for driving the artificial organ, charge status detecting means for detecting a charge status of the storage means, and charge status transmitting means for transmitting outside the body the charge status detected by the charge status detecting means; and
(B) a feeding device provided separately from the storage device and disposed as a whole outside the body, and including a power transmitting coil acting as a primary side coil in said pair of coils, AC output means for outputting AC to the power transmitting coil, charge status receiving means for receiving the charge status transmitted outside the body from said charge status transmitting means, and charge status informing means for informing the charge status received by the charge status receiving means;
wherein the storage device includes an amount of coil displacement detecting means adapted for detecting an extent of a displacement occurring between the power receiving coil and the power transmitting coil (an amount of coil displacement);
the storage device includes a direction of coil displacement detecting means adapted for detecting a direction of a displacement occurring between the power receiving coil and the power transmitting coil (a direction of coil displacement);
the power receiving coil included in the storage device is a detecting element provided for detecting an amount of coil displacement detected by the amount of coil displacement detecting means and a direction of coil displacement detected by the direction of coil displacement detecting means:
a detection result communicating period is set after every fixed charging period, and a circuit operation, in which a digital signal is transmitted from a secondary side control circuit to a digital variable resistor so that the digital variable resistor has a resistance to make a resonant condition by a resonance circuit a virtually absolutely non-resonant condition only for a predetermined short period of time, is repeated so that a number of divided pulses corresponding to a charge voltage and the digital signal, said amount of coil displacement detected by said amount of coil displacement detecting means, and the direction of displacement from the amount of coil displacement may be transmitted outside the body by said charge status transmitting means after said every fixed charging execution period; said charge status transmitting means further transmits outside the body said amount of coil displacement detected by said detecting means and the direction of displacement from the amount of coil displacement; and
said feeding device further includes informing means for informing the charge status of the said storage device, a state of coil displacement and the directions of coil displacement for every receiving signal of the amount of coil displacement.

13. A contactless charging system for an artificial organ as defined in claim 12, wherein
the at least one power transmitting coil comprises four transmitting coils arranged adjacent one another in a plane.

14. A storage apparatus for use with a contactless charging system for an artificial organ adapted to be embedded in a body with the artificial organ, comprising:
a storage device including a power receiving coil acting as a secondary side coil for transferring power, rectifying means for rectifying and outputting an alternating current received by the power receiving coil, storage means for storing output from the rectifying means as electric power for driving the artificial organ, charge status detecting means for detecting a charge status of the storage means, and charge status transmitting means for transmitting outside the body the charge status detected by the charge status detecting means;
wherein the storage device includes amount of coil displacement detecting means for detecting an amount of coil displacement as an extent of a displacement occurring between the power receiving coil and a power transmitting coil,
wherein the amount of coil displacement detecting means of said storage device includes a smoothing circuit for smoothing a voltage at opposite ends of said power receiving coil, and a secondary side control circuit for determining the amount of coil displacement based on a smoothed voltage value, and
wherein an output voltage range of the smoothing circuit is divided into divisions, and wherein the secondary side control circuit determines the amount of coil displacement based on a smoothed voltage by checking a value of a voltage output from the smoothing circuit, recognizing a division corresponding thereto, and detecting the amount of coil displacement based thereon.

15. A feeding apparatus for use with a contactless charging system for an artificial organ embedded inside a body, the feeding apparatus adapted for use outside the body, comprising:
a feeding device including a power transmitting coil acting as a primary side coil, AC output means for outputting AC to the power transmitting coil, charge status receiving means for receiving a charge status transmitted outside the body from said charge status transmitting means, and charge status informing means for informing the charge status received by the charge status receiving means;
wherein the feeding device includes amount of coil displacement detecting means for detecting an amount of coil displacement as an extent of a displacement occurring between a power receiving coil and the power transmitting coil, and the feeding device includes amount of coil displacement informing means for informing the amount of coil displacement detected by the amount of coil displacement detecting means;

wherein the amount of coil displacement detecting means of said feeding device includes a smoothing circuit for smoothing a voltage at opposite ends of said power transmitting coil, and a primary side control circuit for determining the amount of coil displacement based on a smoothed voltage value, and wherein an output voltage range of the smoothing circuit is divided into divisions, and wherein the primary side control circuit determines the amount of coil displacement based on a smoothed voltage by checking a value of a voltage output from the smoothing circuit, recognizing a division corresponding thereto, and detecting the amount of coil displacement based thereon.

* * * * *